United States Patent
Paufique

(10) Patent No.: US 9,333,169 B2
(45) Date of Patent: May 10, 2016

(54) ACTIVE INGREDIENT THAT IS OBTAINED FROM CANDIDA SAITOANA AND COSMETIC USE FOR DETOXIFYING SKIN CELLS

(75) Inventor: Jean Paufique, Objat (FR)

(73) Assignee: SOCIETE INDUSTRIELLE LIMOUSINE D'APPLICATION BIOLOGIQUE dite SILAB, Objat (FR)

( * ) Notice: Subject to any disclaimer, the term of this patent is extended or adjusted under 35 U.S.C. 154(b) by 0 days.

(21) Appl. No.: 13/393,567

(22) PCT Filed: Sep. 3, 2010

(86) PCT No.: PCT/FR2010/051841
§ 371 (c)(1),
(2), (4) Date: Mar. 1, 2012

(87) PCT Pub. No.: WO2011/027085
PCT Pub. Date: Mar. 10, 2011

(65) Prior Publication Data
US 2012/0164121 A1    Jun. 28, 2012

(30) Foreign Application Priority Data
Sep. 4, 2009   (FR) .................................. 09 56041

(51) Int. Cl.
*A61K 8/99* (2006.01)
*A61Q 19/00* (2006.01)
*A61Q 19/08* (2006.01)

(52) U.S. Cl.
CPC . *A61K 8/99* (2013.01); *A61Q 19/00* (2013.01); *A61Q 19/08* (2013.01)

(58) Field of Classification Search
None
See application file for complete search history.

(56) References Cited

U.S. PATENT DOCUMENTS

| | | | |
|---|---|---|---|
| 6,548,075 B1 * | 4/2003 | Bengs et al. ................... | 424/401 |
| 6,616,935 B1 * | 9/2003 | Bengs et al. ................... | 424/401 |
| 2008/0085287 A1 | 4/2008 | Auclair et al. | |
| 2008/0095731 A1 * | 4/2008 | Mitra .......................... | 424/70.13 |
| 2010/0310721 A1 * | 12/2010 | Azuma et al. ................... | 426/62 |

FOREIGN PATENT DOCUMENTS

| | | |
|---|---|---|
| EP | 0093635 | 11/1983 |
| EP | 1629720 | 3/2006 |
| JP | 61238708 | 10/1986 |
| WO | 9107091 | 5/1991 |
| WO | 2006032530 | 3/2006 |

OTHER PUBLICATIONS

Berescada E et al. (2009). Effects of topical gluco-oligosaccharide and collagen tripeptide F in the treatment of sensitive atopic skin. Int J Cosmet Sci., v31(4), p. 271-277—Abstract.*
Ma J et al. (2012). Dectin-1-triggered Recruitment of Light Chain 3 Protein to a Phagosomes Facilitates Major Histocompatibility Complex Class II Presentation of Fungal-derived Antigens. J. Biol. Chem., v287(41), p. 34149-34156.*
Internet article from Blume Skin Care Centre, 6 pages + pub. date. (2005).*
Masuoka (2004). Surface Glycans of Candida albicans and Other Pathogenic Fungi: Physiological Roles, Clinical Uses, and Experimental Challenges. Clinical Microbiology Reviews, v17(2), p. 281-310.*
Bagiyan et al. (1997). The action of alpha-mannosidase from *Oerskovia* sp. on the mannose-rich O-linked sugar chains of glycoproteins. Eur. J. Biochem. v249, p. 286-292.*
Shibata et al. (1996). Structure and Antigenicity of the Mannans of Candida famata and Candida saitoana: Comparative Study with the Mannan of Candida guilliermondii. Archives of Biochemistry and Biophysics, v336(1), p. 49-58.*
WHOIS record for blumeskintreatment.com (record retrieved Apr. 23, 2015 by the examiner).*
Ruszova et al. (2008). Photoprotective effects of glucomannan isolated from Candida utilis. Carbohydrate Research, v343, p. 501-511.*
Suzuki and Nakase (1998). Cellular Neutral Sugar Compositions and Ubiquinone Systems of the Genus *Candida*. Microbiol Cult Coll, v14(2), p. 46-62.*
Tanida et al. (2008). LC3 and Autophagy. Methods Mol Biol, v445, p. 77-88.*
International Search Report dated Mar. 29, 2011, in PCT application.

* cited by examiner

*Primary Examiner* — Scott Long
*Assistant Examiner* — Sean C Barron
(74) *Attorney, Agent, or Firm* — Young & Thompson

(57) ABSTRACT

The object of the invention is the use of *Candida saitoana* or an active ingredient that is obtained from *Candida saitoana* as a cosmetic active ingredient, in particular for the detoxification of skin cells. The invention also relates to an active ingredient that is obtained from *Candida saitoana*, to a production process, as well as to cosmetic compositions that contain this active ingredient, and to a cosmetic personal care process for improving the surface condition of dull and intoxicated skin.

8 Claims, No Drawings

ACTIVE INGREDIENT THAT IS OBTAINED FROM CANDIDA SAITOANA AND COSMETIC USE FOR DETOXIFYING SKIN CELLS

This invention relates to the cosmetic use of *Candida saitoana* as a cosmetic active ingredient, in particular for detoxifying skin cells, as well as a cosmetic personal care process for improving the surface condition of dull and intoxicated skin.

The invention also relates to an active ingredient that is obtained from *Candida saitoana*, a production process, as well as cosmetic compositions that contain this active ingredient.

The skin, organ in contact with the environment, is constantly subjected to damage, both from the outside and from the inside, which threatens its balance and its appearance.

So as to protect and maintain its integrity in the face of this damage, the skin has natural protective systems.

However, when these systems are overstressed or fail, it is no longer protected: it is weakened, intoxicated, and its appearance is modified. It is known, for example, that excessive exposure to ultraviolet rays (UV) is reflected by various cutaneous manifestations, such as actinic erythemas, solar elastosis, or else the premature appearance of the effects of cutaneous aging: the skin becomes loose, deeply wrinkled, rough, dry, sprinkled with hypopigmented or hyperpigmented spots and dilated vessels.

These manifestations, which reflect profound structural changes in the cutaneous tissue, are unsightly and ugly, and many people have a tendency to want to smooth them out.

This is why the objective of this invention is to propose an effective cosmetic means for protecting the skin against damage, both from the outside and from the inside, which can alter its proper operation and its appearance, in particular a means that can stimulate the natural protective systems of skin cells.

The systems for protecting the skin are organized into defense systems, which make it possible to limit the induction of cellular damage by counteracting in particular the reactive radicals of oxygen, and systems for repair and detoxification, which eliminate the already damaged cellular components such as molecules or organelles.

The cells of the skin are equipped in particular with a powerful proteolytic system that consists of two major and complementary mechanisms in the elimination and the detoxification of altered proteins and organelles: the proteasome and autophagy.

The primary function of the proteasome connected to the ubiquitin is to degrade in a targeted manner the soluble proteins with a short service life that are functional and non-functional.

The autophagy that is associated with lysosomes takes charge of the continuous recycling of proteins with a long shelf life and organelles that have become non-functional or obsolete and thus ensures a quality control of the cytoplasm elements. In this method, vacuoles, called autophagosomes, sequester a portion of cytoplasm that contains proteins or organelles that are to be eliminated, and then fuse with the lysosomes that contain proteases that will ensure the degradation of their contents.

These two detoxification entities, by their complementary action, eliminate the various abnormal or superfluous components of the cell, and degrade them into amino acids that will next be recycled for the synthesis of new molecules.

In the case of a moderate oxidative stress, it is primarily the proteasomic degradation system that acts. The oxidized intracellular proteins lose their activity and unfold, becoming a perfect target for degradation by means of the proteasome. In contrast, the autophagy eliminates few cytosolic proteins but concentrates on the altered cellular organelles, with its first target being the mitochondrion for preventing the excessive production of free radicals and the propagation of stress.

In the case of a higher stress or a moderate but repeated stress, the damage is greater. More numerous, the intracellular proteins overload and then exhaust the capacity for degradation of the proteasome and accumulate. They also undergo additional modifications or aggregate: they are then insoluble and cannot be folded and become not only resistant to degradation by means of the proteasome but also act as inhibitors of the latter.

With the capacities of the proteasome being exceeded, authophagy takes over for compensating for its failures and ensuring the degradation of altered soluble proteins while maintaining its role in the elimination of insoluble proteins, oxide lipids, and damaged organelles.

Unfortunately, at a more advanced stage, when the degradation capacities of the autophagy are in turn saturated, the aggregates accumulate and are combined with residues of peroxide lipids or altered organelles to form a non-degradable material, called lipofuscin, which induces the additional production of reactive radicals of oxygen, impacts the effectiveness of proteasomic and autophagic detoxification systems and leads to new cellular damage. This generates a loss of cellular functionality until the cell dies.

In addition, in the event that natural detoxification systems fail, the skin, intoxicated by its own altered components that saturate it little by little, undergoes signs of premature wear and aging.

With the skin being the constant target of potential stress, studies have been conducted on natural systems of cutaneous protection. In particular, products have been developed for the purpose of stimulating the pathway of the proteasome. However, although it is sensitive and can be induced quickly, this system can be easily saturated and then fail.

Thus, to remedy the deficiencies and drawbacks of the prior art, the invention proposes an effective cosmetic approach for the care and protection of the skin, able to act in particular on the autophagy of the skin cells.

For this purpose, the invention proposes using a yeast, *Candida saitoana*, as a cosmetic active ingredient.

*Candida saitoana* is a known yeast, primarily used in the biological fight to ensure the protection and the preservation of fruits after their harvest.

However, surprisingly enough, *Candida saitoana* has significant effects on the skin with very advantageous cosmetic properties.

The purpose of the invention is therefore the use of *Candida saitoana* or an active ingredient that is obtained from *Candida saitoana* as a cosmetic active ingredient, designed to be applied on the skin, in particular for stimulating autophagy, an essential system for freeing skin cells from all of the damage that can engorge them and prevent their proper operation.

The purpose of the invention is also a cosmetic active ingredient that is obtained from *Candida saitoana* that comprises in particular carbohydrates, primarily in the form of α-glucan oligosaccharides, as well as a process for the production of this active ingredient, and cosmetic compositions that include at least one such active ingredient.

The active ingredients according to the invention can be obtained by a process that comprises a stage for solubilization of *Candida saitoana* (obtained by fermentation) followed by at least one enzymatic hydrolysis stage in such a way as to obtain an active ingredient that comprises carbohydrates.

In a preferred manner, the cosmetic compositions according to the invention contain 0.01 to 20% of an active ingredient that is obtained from *Candida saitoana* and that comprises carbohydrates that for the most part are in the form of α-glucan oligosaccharides.

The administration of a composition that contains an active ingredient that is obtained from *Candida saitoana* according to the invention is implemented by topical means. The compositions according to the invention can come in all forms that allow the application by topical means.

Finally, the invention also has as its object a cosmetic personal skin care process that is designed to improve the surface condition of dull and/or intoxicated skin, in particular designed to smooth the microrelief of the skin and/or to improve complexion brightness.

This invention is now described in detail.

Active Ingredient

The purpose of the invention is therefore the use of *Candida saitoana* or a *Candida saitoana* extract as a cosmetic active ingredient.

The invention also relates to a particular cosmetic active ingredient that is obtained from *Candida saitoana* and that comprises carbohydrates.

Preferably, it is an active ingredient that is obtained from *Candida saitoana* that has a carbohydrate content of at least 28% of the total weight of dry material, in particular a carbohydrate content that is between 28% and 67% of the total weight of the dry material.

Even more preferably, at least 20% of the carbohydrates that are present in the active ingredient are in the form of α-glucan oligosaccharides.

The active ingredient according to the invention preferably comes in liquid form. It can be defined by at least one—preferably all—of the characteristics disclosed below.

Dry Materials:

The level of dry materials of an active ingredient that is obtained from *Candida saitoana* according to the invention, measured by passing through the oven at 105° C. in the presence of sand until a constant weight is obtained, is between 7 and 125 g/l, preferably between 30 and 45 g/l.

Measurement of pH:

The pH that is measured by the potentiometric method at ambient temperature leads to values of between 2.5 and 5.5, preferably between 3.0 and 4.0.

Determination of the Total Sugar Content

The DUBOIS method is used. In the presence of concentrated sulfuric acid and phenol, the reducing sugars provide an orangey-yellow compound. Starting from a standard range, it is possible to determine the level of carbohydrates of an active ingredient according to the invention.

The level of carbohydrates of an active ingredient that is obtained from *Candida saitoana* according to the invention, measured by the DUBOIS method, is between 3 and 56 g/l, preferably between 13 and 20 g/l.

The active ingredient contains at least 28% carbohydrates relative to the total dry materials. Preferably, the content is between 28 and 67%.

Characterization of Carbohydrates

The analysis by HPLC of an active ingredient according to the invention makes it possible to determine the distribution of the molecular weights of the glucidic fraction.

|  | Molecular Weight (Da) | Percentage of the Glucidic Fraction of an Active Ingredient According to the Invention (%) |
|---|---|---|
| Monosaccharides | <180 | Between 50 and 60% |
| Oligosaccharides | 180 < MM < 1,500 | Between 40 and 50% |

The mean molar mass of the oligosaccharide fraction is 885 Da, or a mean degree of polymerization of 5.

The characterization by gas phase chromatography (GPC) of the glucidic fraction of the active ingredient according to the invention provides the following results:

|  | Composition of the Glucidic Fraction of an Active Ingredient According to the Invention (Percent by Mass %) |
|---|---|
| Glucose | 95.4 |
| Mannose | 2.3 |
| N-Acetylglucosamine | 2.3 |

The dosage of glucans by a "mushroom and yeast beta-glucan" kit (reference K-YBGL, megazyme) of the glucidic fraction of the active ingredient according to the invention provides the following results:

|  | Percentage of the Components |
|---|---|
| β-Glucans | Between 30 and 40% |
| α-Glucans | Between 60 and 70% |

An active ingredient that is obtained from *Candida saitoana* according to the invention is therefore characterized by a carbohydrate fraction that consists of:
- 40 to 50% oligosaccharides having a mean degree of polymerization of 5, of which 30 to 40% are β-glucan oligosaccharides β-1,3 and β-1,6) and 60 to 70% are α-glucan oligosaccharides,
- 50 to 60% monosaccharides, in the form of glucose, mannose and N-acetyl glucosamine.

Active Fraction

The active fraction of an active ingredient that is obtained from *Candida saitoana* according to the invention has been determined by comparing the capacity of different molecular fractions of the active ingredient, to simulate the synthesis of LC3, specific marker of autophagosomes.

The results of this study well show that these are essentially sugars that impart to the active ingredient that is obtained from *Candida saitoana* its cosmetic activity on the autophagy, in particular the α-glucan oligosaccharides, and even more particularly the α-glucan trisaccharides.

Production Process

The purpose of this invention is also a process for the production of an active ingredient that is obtained from *Candida saitoana*.

It involves a process that makes it possible to concentrate the active ingredient in terms of sugars, in particular in terms of α-glucan oligosaccharides. It comprises at least the following stages:
Cultivation of *Candida saitoana* yeasts,
Aqueous solubilization of the yeasts that are obtained, At least one enzymatic hydrolysis for the purpose of producing oligosaccharides, Deactivation of enzymatic activity by heat treatment, Separation of soluble and insoluble phases, Concentration of the soluble phase for recovering an active fraction that comprises sugars, preferably an active fraction that comprises sugars of which at least 20% are in α-glucan oligosaccharide form.

One particularly suitable embodiment of the invention comprises the following stages:

Cultivation of *Candida saitoana* yeasts in a standard manner in a medium that is suitable for their development, preferably in the presence of saccharose, Harvest of yeasts by centrifuging, then freezing yeasts (for preservation), Solubilization of yeasts harvested in an aqueous solution, Production of at least one enzymatic hydrolysis for the purpose of producing oligosaccharides, Deactivation of enzymatic activity by heat treatment, Centrifuging or filtering in such a way as to remove most of the insoluble membrane components and to collect a filtrate that is rich in compounds of a carbohydrate nature, namely a fraction that comprises at least 28% carbohydrates relative to the total weight of the dry material, including at least 20% in the form of α-glucan oligosaccharides.

Additional stages of filtration and sterilizing filtration can be considered.

Preferably, the enzymatic hydrolysis is implemented in the presence of one or more carbohydrates, proteases and/or lipases.

The active ingredient that is obtained comes in the form of a clear liquid aqueous solution that is clear yellow in color.

Use

The invention also relates to the use of *Candida saitoana* or a *Candida saitoana* extract as a cosmetic active ingredient, in particular the use of *Candida saitoana* or a *Candida saitoana* extract as a cosmetic active ingredient that is an activator of the autophagy of skin cells in or for the preparation of a cosmetic composition.

According to the invention, *Candida saitoana* or an active ingredient that is obtained from *Candida saitoana* can actually be used as a cosmetic agent on the skin for activating the autophagy of skin cells for the purpose of their detoxification. The presence of a sufficient quantity of carbohydrates, in particular α-glucan oligosaccharides, even more particularly α-glucan trisaccharides, in the *Candida saitoana* active ingredient, makes it possible in particular to impart this cosmetic activity to it.

When it is applied on the skin, *Candida saitoana* or an active ingredient that is obtained from *Candida saitoana* can stimulate the pathway of the autophagy of the skin cells. In particular, it is capable of acting on the synthesis of the LC3 protein, specific marker of the autophagosome.

The autophagy is a "partial self-digestion" process that consists of a degradation of intracellular components by lysosome. There are three types of autophagy: microautophagy, autophagy that is mediated by chaperone proteins and macroautophagy, with the latter two being purely connected to stress.

The macroautophagy is the primary form of autophagy and the least selective. Its mechanism comprises several stages:

The formation of a multi-membrane structure, called a phagophore or preautophagosome, which elongates for sequestering the cytoplasmic material that is to be degraded, thus forming an autophagy vacuole or autophagosome, The fusion between this vacuole and the lysosome for allowing the degradation of the content that is to be eliminated by the lysosomal enzymes.

The molecular system that is responsible for the autophagy is under the control of the ATG genes ("autophagy-related genes"). During the formation of the autophagosome, the ATG proteins are engaged from the cytoplasm and are temporarily combined with the autophagosomal membrane. The Beclin 1 (ATG6)-phosphatidyl inositol 3-phosphatase complex initiates the formation of the autophagosome. It allows the sequential engagement of the cytosolic conjugates ATG12-ATG5 and LC3 ("Light Chain 3" or ATG8) at the autophagosomal membrane. The engaged LC3-I protein is covalently linked to a phosphatidyl ethanolamine, a lipid of the autophagosomal membrane, for forming the LC3-II form. All of the ATG proteins are quickly separated, except for the LC3-II protein that remains combined with the membrane of the autophagosome and that is responsible for the size of the autophagosome that is formed.

The dysfunction of autophagy can lead to the formation of fewer autophagic vacuoles, to a reduction in their fusion with the lysosomes, and to a reduction in their elimination after they have fused. The non-degraded material accumulates inside the lysosome in the form of lipofuscin, which can deactivate the enzymes of lysosome or destabilize its membrane, leading to additional cellular damage.

However, used on the skin, *Candida saitoana* or an active ingredient that is obtained from *Candida* makes it possible to boost the pathway of the autophagy of the skin cells. In particular, it stimulates the synthesis of the LC3 protein. Advantageously, by stimulating the formation of the autophagosome that is responsible for sequestering the altered cellular components and for orienting them toward the pathway of lysosomal degradation, it thus makes it possible to remove pollution from the cells of the altered components that saturate them, source of accelerated aging.

*Candida saitoana* or an active ingredient that is obtained from *Candida saitoana* can thus be used for reinforcing the detoxification of the skin cells, in particular for reducing the level of oxidized proteins and peroxide lipids.

Actually, all of the amino acids that compose the proteins can be oxidized, with the sulfur-containing and aromatic amino acids being the most sensitive. Their oxidation leads to the formation of hydroxyl groups on the side chains of the proteins that can result in the fragmentation of polypeptide chains or to intra- or inter-molecular cross-linkings. In the case of freer oxidation, carbonyl derivatives are generated by oxidation that is catalyzed by metals or certain amino acids, or by cleavage of proteins. In addition, secondary reactions that use oxidation and involve the attachment—to the proteins—of glucids or aldehydes that are derived from lipidic peroxidation can be grafted onto these so-called direct modifications.

There are specific systems for reversal of the oxidation of sulfur-containing amino acids, but the oxidation of other amino acids as well as carbonylation lead to irreversible modifications of the structure of proteins that accumulate and aggregate with age or in the case of prolonged or repeated damage to the skin. If these aggregates are not eliminated, they can lead to significant damage. It is known in particular that the presence of carbonyl proteins on the horny layer affects its properties: the barrier function is degraded, the mechanical properties are modified, the fibrous structure of the keratin is transformed, and the optical properties of the stratum corneum are altered, impacting the quality of appearance of the skin.

Furthermore, the formation of lipidic hydroperoxides results from the attack of free radicals at a double bond of a polyunsaturated fatty acid. In the presence of oxygen, chain reactions follow, giving rise to numerous compounds of different structures, such as aldehydes of which malonic dialdehyde [is] particularly reactive with the amino acids lysine and cysteine for forming carbonyl proteins. The lipoperoxides also have significant effects on the stability and the permeability of cellular membranes.

Advantageously, *Candida saitoana* or an active ingredient that is obtained from *Candida saitoana* that is used on the skin stimulates the elimination by the pathway of the autophagy of oxidized proteins and/or peroxide lipids.

*Candida saitoana* or an active ingredient that is obtained from *Candida saitoana* thus plays a role in the process of cellular detoxification and participates in moderating the phenomena involved in the cutaneous aging.

Advantageously, the invention can therefore be used for improving the surface condition of the skin, in particular for smoothing the skin microrelief and improving complexion brightness. *Candida saitoana* or an active ingredient that is obtained from *Candida saitoana* actually makes it possible to regenerate dull and intoxicated skin for improving its surface condition: applied on the skin, it has a restorative and detoxifying effect. The facial features are visibly smoothed; the brightness of the intoxicated and worn skin is revived.

Cosmetic Compositions and Cosmetic Process for Personal Skin Care

This invention also covers the cosmetic compositions that include at least one active ingredient that is obtained from *Candida saitoana* and that has a carbohydrate content of at least 28%, in different galenical forms, adapted to the administration by cutaneous topical means.

These compositions can come in particular in the form of oil-in-water emulsions, water-in-oil emulsions, multiple emulsions (water/oil/water or oil/water/oil) that can optionally be microemulsions or nanoemulsions, or in the form of solutions, suspensions, hydrodispersion, aqueous gel or powders. They can be more or less fluid and have the appearance of a cream, a lotion, a milk, a serum, an ointment, a gel, a paste or a foam, or they can be in solid form.

These compositions contain between 0.01 and 20% by weight of active ingredient(s) that is/are obtained from *Candida saitoana* according to this invention, preferably between 0.5% and 3%.

These compositions comprise, in addition to the active ingredient, a physiologically acceptable medium, and preferably a cosmetically acceptable medium, i.e., that does not cause unacceptable feelings of discomfort for the user such as flushing, tingling or tickling. This medium generally contains water.

The compositions according to the invention can contain—as an adjuvant—at least one compound that is selected from among:

Oils, which can be selected in particular from among the silicone oils that are linear or cyclic, volatile or non-volatile;
Waxes, such as ozokerite, polyethylene wax, beeswax, or carnauba wax;
Silicone elastomers,
Surfactants, preferably emulsifying surfactants, whether they are non-ionic, anionic, cationic or amphoteric,
Co-surfactants, such as linear fatty alcohols,
Thickeners and/or solidifiers,
Moisturizers, such as the polyols such as glycerin,
Organic filters,
Inorganic filters,
Dyes, preservatives, feedstocks,
Tightening agents,
Sequestering agents,
Perfumes, and
Mixtures thereof, without this list being limiting.

Examples of such adjuvants are cited in particular in the Dictionnaire CTFA (International Cosmetic Ingredient Dictionary and Handbook, published by the Personal Care Product Council).

These compositions are designed in particular for the personal care, the treatment and the protection of human skin against the effects of various types of damage, both from the inside and from the outside, in particular for the cellular detoxification and the improvement of the surface condition of the skin.

The purpose of the invention in this respect is a cosmetic process for personal care of the human skin, designed to improve the surface condition of dull and/or intoxicated skin, comprising the topical application on the skin of a composition that contains an active ingredient that is obtained from *Candida saitoana*, in particular a composition that contains between 0.01 and 20% by weight of the active ingredient(s) that is/are obtained from *Candida saitoana* according to this invention.

The purpose of the invention is also a cosmetic process for personal care of the human skin, designed to smooth the microrelief of the skin and/or to improve complexion brightness, comprising the topical application on the skin of a composition that contains an active ingredient that is obtained from *Candida saitoana*, in particular a composition that contains between 0.01 and 20% by weight of the active ingredient(s) that is/are obtained from *Candida saitoana* according to this invention.

It is possible to cite formulations that have shown a physical stability that includes 5% of an active ingredient according to the invention. The stability is characterized by an absence of precipitation of the extract, an absence of creaming, and an absence of phase shift.

Clear gel:
  Carbopol: 0.5% with triethanolamine: enough to produce pH=6.5
  Glycerol: 10.0%
  Propylene glycol: 10.0%
  Preservative: 1.0%
  Active ingredient that is obtained from *Candida saitoana* according to the invention: 5.0%
  Water: 73.5%
Opaque gel:
  Sepigel 305: 3.0%
  Lanol 99: 12.0%
  Preservative: 1.0%
  Active ingredient that is obtained from *Candida saitoana* according to the invention: 5.0%
  Water: 79.0%
Emulsified gel:
  Montanov 202: 3.0%
  Isopropyl palmitate: 10.0%
  Sepigel 305: 2.0%
  Preservative: 1.0%
  Active ingredient that is obtained from *Candida saitoana* according to the invention: 5.0%
  Water: 79.0%
Non-ionic emulsion:
  Montane 60: 2.0%
  Montanox 60: 4.0%
  Isopropyl myristate: 8.0%
  Paraffin wax 130/135: 3.0%

Preservative: 1.0%
Active ingredient that is obtained from *Candida saitoana* according to the invention: 5.0%
Water: 77.0%

Anionic emulsion:
Stearic acid: 7.0% triethanolamine, enough to produce pH=8
Ritaphyl ICS: 20.0%
Preservative: 1.0%
Active ingredient that is obtained from *Candida saitoana* according to the invention: 5.0%
Water: 67.0%

Cationic emulsion:
Quaternium-82: 5.0%
Cetyl alcohol: 1.0%
Gemseal 60: 8.0%
Cetearyl alcohol: 1.0%
PEG 100 stearate: 1.0%
Preservative: 1.0%
Active ingredient that is obtained from *Candida saitoana* according to the invention: 5.0%
Water: 78.0%

Tests have shown the compatibility of the active ingredient with the raw materials that are used in cosmetics: thickeners, emulsifiers, solvents.

Of course, one skilled in the art will ensure the selection of the possible complementary active or non-active compounds and/or their quantity in such a way that the advantageous properties of the mixture are not, or are essentially not, altered by the addition that is under consideration.

EXAMPLES

Examples of Active Ingredients According to the Invention

Example 1

The active ingredient of Example 1 has the following characteristics:
Aqueous solution
Appearance: clear liquid
Color: clear yellow
pH: 3.8
Dry materials: 36.4 g/l
Total sugar content: 16.3 g/l or 45% by weight of dry material
α-Glucan content: 27.9% by weight relative to the total carbohydrates.

It is produced by the implementation of the following stages:
Solubilization of *Candida saitoana* in water at a rate of 30 g/l,
Enzymatic hydrolysis using a carbohydrase,
Deactivation by heat treatment,
Separation of soluble and insoluble phases,
Concentration of the soluble phase and filtrations in such a way as to separate the majority of the insoluble membrane components and to collect a filtrate that comprises 45% carbohydrates by weight of dry material of which 27.9% is in the form of α-glucan oligosaccharides,
Sterilizing filtration.

Example 2

The active ingredient of Example 2 has the following characteristics:
Aqueous solution
Appearance: clear liquid
Color: clear yellow
pH: 4.3
Dry materials: 36.6 g/l
Total sugar content: 18.7 g/l or 50% by weight of dry material
Protein content (determined by the LOWRY method—Lowry et al., Protein Measurement with Folin Reagent, Journal Biol. Chem., 193, 265): 6.6 g/l or 18% by weight of dry materials
Ash content: 9.1 g/l or 25% by weight of dry material
α-glucan content: at least 20% by weight relative to the total carbohydrates.

It is obtained by the implementation of the following stages:
Solubilization of *Candida saitoana* in water at a rate of 40 g/l,
Enzymatic hydrolysis using a carbohydrase,
Deactivation by heat treatment,
Separation of soluble and insoluble phases,
Concentration of the soluble phase and filtrations in such a way as to remove the majority of the insoluble membrane components and to collect a filtrate that comprises 50% carbohydrates by weight of dry material including at least 20% in the form of α-glucan oligosaccharides,
Sterilizing filtration.

Examples of Cosmetic Compositions

It is also possible to cite examples of cosmetic compositions that include the active ingredient according to the invention. The following examples of compositions are obtained by mixing different components. The quantities that are indicated are provided by percentage of weight.

Example 3

Night Cream

The formulation is as follows:

| | | |
|---|---|---|
| A. | Water | Enough to make 100% |
| | Propylene glycol | 10% |
| | Carbopol 2050 (Noveon) | 0.2% |
| B. | DUB MCT 5545 (Stéarinerie Dubois) | 10% |
| | DUB liquid 85 (Stéarinerie Dubois) | 6% |
| | DUB wax A (Stéarinerie Dubois) | 2% |
| | DUB G1218A (Stéarinerie Dubois) | 3% |
| | DUB 1632 (Stéarinerie Dubois) | 2% |
| | DC 200 (Dow Corning) | 2% |
| C. | Preservative | 1% |
| | Active ingredient that is obtained from *Candida saitoana* according to the invention | 3% |
| D. | NaOH | 0.5% |

This cream has a pH of 5.
It can be obtained by the implementation of the following stages:
Mixing A, heating to 60° C. and thoroughly dispersing the gel while being stirred mechanically until the carbopol is completely dissolved,
Heating A and B to 80° C., while being stirred mechanically,
Emulsifying B in A under an emulsifying agent, Adding C in order at 40° C. and homogenizing,
Adjusting the pH with D at 30° C.,
Continuing the homogenization until the cream is uniform.

Example 4

Anti-Aging Day Cream

The formulation is as follows:

| A. | Water | Enough to make 100% |
|---|---|---|
| | Carbopol Ultrez 20 (Noveon) | 0.3% |
| | Glycerol | 3% |
| | EDTA | 0.2% |
| B. | Sophim MC30 (Sophim) | 6% |
| | DUB MCT5545 (Stéarinerie Dubois) | 5% |
| | Karite butter (Sictia) | 3% |
| | Sterol CC/595 (Cesalpina) | 3% |
| | Ritapro 165 (Rita) | 3% |
| | DC 345 (Dow Corning) | 1% |
| | DUB zenoate (Stéarinerie Dubois) | 2% |
| C. | Preservative | 1% |
| | Active ingredient that is obtained from *Candida saitoana* according to the invention | 3% |
| D. | TEA | Enough to produce pH = 5.3 |

This emulsified gel has a pH of 5.3.
It can be obtained by the implementation of the following stages:
Mixing A,
Mixing B,
Heating A and B to 80° C. while being stirred mechanically,
Emulsifying B in A while being stirred,
Adding C in order at 50° C. and homogenizing,
Continuing the homogenization by adding D until the mixture is uniform, and
Allowing it to cool to 30° C. while being stirred.

Example 5

Serum

The formulation is as follows:

| A. | Water | Enough to make 100% |
|---|---|---|
| | Glycerol | 3% |
| | Carbopol ETD 2050 (Noveon) | 0.3% |
| | Butylene glycol | 5% |
| B. | DUB ININ (Stéarinerie Dubois) | 3% |
| | Arlamol E (Noveon) | 3% |
| | DUB PTIS (Stéarinerie Dubois) | 2% |
| | DUB PTCC (Stéarinerie Dubois) | 3.3% |
| C. | Preservative | 1% |
| | Active ingredient that is obtained from *Candida saitoana* according to the invention | 3% |
| D. | NaOH | Enough to produce pH = 6.5 |

This serum has a pH of 6.5.
It can be obtained by the implementation of the following stages:
Mixing A, by thoroughly dispersing the gel while being stirred mechanically,
Mixing B,
Heating A and B to 80° C.,
Emulsifying B in A under an emulsifying agent,
Adding C in order at 40° C., and homogenizing,
Adjusting the pH with D, while being stirred mechanically,
Continuing the homogenization until the serum is uniform,
Allowing stirring to continue until cooling to 30° C.

Example 6

Emulsion

The formulation is as follows:

| A. | Water | Enough to make 100% |
|---|---|---|
| | Lanol 99 (Seppic) | 5% |
| | Sepigel 305 (Seppic) | 0.3% |
| B. | Montanov 202 (Seppic) | 3% |
| | Montanov 68 (Seppic) | 2.0% |
| C. | Preservative | 0.7% |
| | Active ingredient that is obtained from *Candida saitoana* according to the invention | 3% |

It can be obtained by the implementation of the following stages:
Mixing A, by thoroughly dispersing the gel while being stirred mechanically,
Mixing B,
Heating A and B to 80° C.,
Emulsifying B in A under an emulsifying agent,
Adding C in order at 40° C. and homogenizing,
Adjusting the pH, while being stirred mechanically,
Continuing the homogenization until the serum is uniform,
Allowing stirring to continue until cooling to 30° C.

Evaluation of the Cosmetic Effect of *Candida saitoana*

Tests have been conducted to show the claimed effects.

1/Evaluation of the Effect on the Pathway of the Autophagy

This first study has as its objective to evaluate in vitro the effectiveness of an active ingredient that is obtained from *Candida saitoana* according to Example 1 and/or Example 2 on the synthesis of the protein LC3, specific marker of autophagic vacuoles, the autophagosomes.

The study was done by Western Blot and by immunocytology respectively on human keratinocytes and on normal HaCat keratinocytes, whose autophagy was induced by a moderate dose of $H_2O_2$.

The operating procedure is described below.

The keratinocytes are first inoculated in a culture medium and incubated at 37° C. in an atmosphere that contains 5% $CO_2$.

After 48 hours of incubation, the culture medium is eliminated and replaced by a culture medium that may or may not contain the active ingredient that is obtained from *Candida saitoana* at 0.50% and 1% (VAT). The cells are then incubated for 3 hours.

After incubation, the culture medium is eliminated and replaced:
For normal cells:
By the culture medium for one part (control), or
A culture medium that contains the active ingredient that is obtained from *Candida saitoana* at 1% (V/V), for another part.
For "autophagy-induced" cells:
An $H_2O_2$ solution at 250 µm for another part (control), or
A culture medium that contains the active ingredient that is obtained from *Candida saitoana* at 0.50% (V/V), for another part.

A culture medium that contains the active ingredient that is obtained from *Candida saitoana* at 1% (V/V) for a third part.

The keratinocytes are incubated again. After 3 hours, the culture media are eliminated and replaced by a culture medium that may or may not contain the active ingredient that is obtained from *Candida saitoana* at 0.50% and 1% (V/V).

The cells are incubated again for 90 minutes, and then the cellular extracts are recovered and stored.

a—Quantification by Western Blot

Electrophoresis on SDS-polyacrylamide gel and immunomarking are done, and then the semi-quantified bands are visualized by densitometry after image analysis using multi-gauge software.

The results that are obtained are presented as a percentage of LC3 synthesis relative to the control, in the following table:

|  | Synthesis of LC3 (%) |
|---|---|
| Normal Cells | |
| Control | 100 |
| Active Ingredient that is Obtained from 1% *Candida saitoana* (Example 1) | 99 |
| "Autophagy-Induced" Cells | |
| Control | 238 |
| Active Ingredient That is Obtained from 0.5% *Candida saitoana* (Example 1) | 255 |
| Active Ingredient That is Obtained from 1% *Candida saitoana* (Example 1) | 284 |

It is therefore noted that tested at 1% on keratinocytes, an active ingredient that is obtained from *Candida saitoana* makes it possible to boost by 19% the synthesis of LC3, specific marker of autophagy.

b—Visualization by Immunocytology

An immunomarking is done, and the results are displayed on a microscope that is coupled to an image analysis system.

The intensity of the marking of the LC3 proteins is proportional to the intensity of green fluorescence that is present at the cytoplasmic level of the cells. The more intense the color green, the higher the rate of synthesis of LC3. The cell nuclei appear to be blue-colored.

With the immunocytological results being qualitative, 4 levels of synthesis of LC3 have been defined:

Very weak detection of immunoreactivity (very pale green color) –

Weak detection of immunoreactivity (pale green color) +

Mean detection of immunoreactivity (mean green color) ++

Strong detection of immunoreactivity (intense green color) +++

The results that are obtained are summarized in the table below:

|  | Synthesis of LC3 |
|---|---|
| Normal Cells | |
| Control | – |
| Active Ingredient that is Obtained from 1% *Candida saitoana* (Example 1) | – |
| "Autophagy-Induced" Cells | |
| Control | + |
| Active Ingredient That is Obtained from 1% *Candida saitoana* (Example 1) | +++ |
| Active Ingredient That is Obtained from 1% *Candida saitoana* (Example 2) | +++ |

These results confirm those obtained by Western Blot and duly show that an active ingredient that is obtained from *Candida saitoana* makes it possible to increase the autophagic activity of skin cells that is initially triggered by a moderate dose of $H_2O_2$.

2/Evaluation of the Effect on Cellular Detoxification

The skin, by its barrier role against environmental damage, is continually exposed to oxidative stress. The proteins are able to be targets of oxidative stress and thus to undergo structural alterations due to the latter.

The carbonylation of proteins (addition of a carbonyl group $C=O$) can take place by oxidative cleavage of proteins or by direct oxidation of certain aminated residues. The reaction with aldehydes that are derived from lipidic peroxidation is also the cause of the formation of these carbonyl groups. This modification of the structure of proteins is irreversible and participates in the premature aging of the skin as well as in the reduction of the transmission of light from the stratum corneum, modifying the quality of the appearance of the skin.

2.a In-Vivo Study of the Effect on the Level of Oxidized Proteins

This study has as its objective to evaluate in vivo the influence of an active ingredient that is obtained from *Candida saitoana* according to Example 1, formulated with 3% in emulsion of Example 6 on the formation of oxidized proteins induced by environmental factors at the level of the stratum corneum.

The study was carried out vs. placebo on 19 healthy volunteers, selected according to an "intoxicated" skin criterion, characterized by high levels of proteins and oxide lipids.

Actually, a prior study conducted on two groups of volunteers: the first group (35 volunteers) corresponding to individuals who have a bright complexion, the second group (37 volunteers) corresponding to individuals who have a dull complexion—made it possible to demonstrate a significant difference in the level of proteins and oxide lipids between the group of individuals with a dull complexion and that of individuals who have a bright complexion (respectively +13% and +33% variation relative to the bright complexion).

The marking of the oxidized proteins was carried out on stratum corneum samples taken using an adhesive on the cheeks before and after 14 days of twice-daily applications.

The operating procedure is as follows.

For 14 days, the volunteers apply a placebo on the face twice daily.

On $D_0$, samples are taken from the cheeks of each volunteer.

The volunteers apply the composition that comprises the active ingredient of *Candida saitoana* and the placebo twice daily.

On $D_{14}$, a last sample is taken from the cheeks of each volunteer.

The oxidized proteins are directly marked on the adhesive that is sampled on the volunteer using a fluoroesceine-5-thiosemicarbazide (FTZ) solution, specific marker of carbonyl groups. This marking makes it possible to evaluate the quantity of oxidized proteins that are present on the surface of the skin. The higher the level of oxidized proteins of the stratum corneum sample, the more intense the fluorescence will be in the green wavelength. The fluorescence is observed using a fluorescence microscope equipped with a camera that is coupled to image analysis software.

The variations that are observed under the action of the tested product vs. placebo are calculated by percentage starting from mean values.

The overall results show that after 14 days of twice-daily applications and in comparison to the placebo, the active ingredient that is obtained from *Candida saitoana*, formulated with 3% in emulsion, reduces the quantity of oxidized proteins by 13.9%.

By limiting the quantity of oxidized proteins, the active ingredient that is obtained from *Candida saitoana* promotes the cellular detoxification.

2.b In-Vivo Study of the Effect on the Level of Peroxide Lipids

The aging is a multifactorial process that is linked to an accumulation of skin damage. Environmental damage and radical types produced during cellular metabolism are the cause of oxidative stress that is involved in the premature aging of the skin. This oxidative stress generates, i.a., the formation of peroxide lipids on cellular membranes and lipoproteins.

The objective of this study is to evaluate in vivo the anti-lipoperoxidizing effect of an active ingredient that is obtained from *Candida saitoana* of Example 1, formulated with 3% in emulsion (Example 6) vs. placebo on the cheeks.

The study was carried out vs. placebo on 19 healthy volunteers, selected according to a criterion of intoxicated skin, i.e., high levels of proteins and oxide lipids.

The anti-lipoperoxidizing effect was evaluated by dosing with peroxide lipids on samples of stratum corneum taken using an adhesive on the cheeks before and after 14 days of twice-daily applications.

The operating procedure is as follows.

For 14 days, the volunteers apply a placebo to their faces twice daily.

On $D_0$, samples are taken from the cheeks of each volunteer, and the samples are stored at $-20°$ C.

The volunteers apply the composition that comprises the active ingredient of *Candida saitoana* and the placebo twice daily.

On $D_{14}$, a final sample is taken from the cheeks of each volunteer, and the samples are stored at $-20°$ C.

The peroxide lipids are sampled using absolute ethanol. The peroxide lipids are dosed by a spectrophotometric method with an absorbance of 500 nm, by using a range of calibration of peroxide lipids at different concentrations.

The variations that are observed under the action of the product vs. placebo are calculated by percentage starting from mean values.

The overall results show that after 14 days of twice-daily applications and in comparison to the placebo, the active ingredient that is obtained from *Candida saitoana* and that is formulated with 3% in emulsion reduces the quantity of peroxide lipids by 23.4%.

By limiting the quantity of peroxide lipids, the active ingredient that is obtained from *Candida saitoana* reinforces the cellular detoxification process.

3/Evaluation of the Effect on the Skin Microrelief

This study has as its object to evaluate in vivo the smoothing effect of an active ingredient that is obtained from *Candida saitoana* of Example 1, formulated with 3% in emulsion (Example 6) vs. placebo on the cheeks by fringe spraying.

The study was carried out on 19 healthy volunteers who were selected according to a criterion of intoxicated skin, i.e., high levels of proteins and oxide lipids.

Imprints were made on the cheeks before and after 14 days of twice-daily treatment and analyzed by fringe spraying.

The operating procedure is as follows.

For 14 days, the volunteers apply a placebo on their faces twice daily.

On $D_0$, imprints are made on the cheeks of each volunteer.

The volunteers apply the composition that comprises the active ingredient of *Candida saitoana* and the placebo twice daily.

On $D_{14}$, imprints are made again on the cheeks of each volunteer.

By analyzing the imprints, the effect is measured over a region of interest of 10 mm$^2$ that is automatically cut out on the original acquisition. The most pertinent parameters that are retained for this study are 3D roughness parameters:

Sq: quadratic mean of surface roughness,

Sa: arithmetic mean of surface roughness.

A reduction of these different parameters is characteristic of a smoothing of the surface that is being studied.

The variations that are observed under the action of the tested product vs. placebo are calculated by percentage starting from mean values.

The overall results after 14 days of twice-daily applications are presented in the following table:

|  | Variation/Placebo (%) |
| --- | --- |
| Sa Parameter | −6.2% |
| Sq Parameter | −7.0% |

These results show well that under the conditions of this study, after 14 days of twice-daily applications and in comparison to the placebo, an active ingredient that is obtained from *Candida saitoana* according to the invention that is formulated with 3% in emulsion smoothes the skin microrelief on the cheeks.

4/Evaluation of the Effect on the Complexion Brightness

The objective of this study is to evaluate in vivo the influence of an active ingredient that is obtained from *Candida saitoana* of Example 1 that is formulated with 3% in emulsion (Example 6) vs. placebo on the complexion brightness.

The complexion brightness is a subjective concept, nevertheless admitted by all, that rests on the reflection of light on the skin. The brightness of the complexion is influenced by different parameters such as lifestyle or environment. The oxidative stress that is linked to environmental damage brings about the alteration of different molecular structures such as proteins and thus participates in the alteration of the appearance of the skin by acting on the reduction of the transmission of light from the stratum corneum.

This study was implemented on 19 healthy volunteers who were selected according to a criterion of intoxicated skin, i.e., high levels of proteins and oxide lipids.

The evaluation of the brightness of the complexion was done blind by a trained expert, before and after 14 days of twice-daily applications.

The operating procedure is as follows.

For 14 days, the volunteers apply a placebo to their faces twice daily.

On $D_0$, an expert evaluates the complexion brightness.

The volunteers apply the composition that comprises the active ingredient of *Candida saitoana* and the placebo twice daily.

On $D_{14}$, an evaluation of the complexion brightness is done.

The evaluation of the complexion brightness is done starting from scales of scores (from 1 to 10) for the following parameters:

The radiation of the skin, characteristic of a bright complexion: the greater the intensity of the catchers of light on the projecting zones of the face, the more luminous the skin, The transparency of the skin, which makes it possible to see the veinlets through the skin: the finer the skin, the more it allows the light to pass, which provides an effect of a good appearance, The clear rose color, which makes it possible to characterize a bright complexion: the rosier the complexion, the more it is perceived as fresh, The olive color, a parameter that is representative of the effect of a good appearance: if the olive color decreases, the effect of a good appearance is more significant.

The evaluation of these parameters is done on the following zones: cheekbones, forehead, chin, and eyes.

The variations that are observed under the action of the tested product vs. placebo are calculated by percentage starting from mean values.

The overall results are presented in the following table:

|  | Variation/ Placebo (%) |
| --- | --- |
| Radiation | +8% |
| Transparency | +9.4% |
| Rose Color | +10.7% |
| Olive Color | −8.3% |

It is noted that after 14 days of twice-daily applications in comparison to the placebo, an active ingredient that is obtained from *Candida saitoana*, formulated with 3% in emulsion, improves the complexion brightness:

It increases the radiation and the transparency of the skin,
It increases the rose color and reduces the olive color.

The active ingredient that is obtained from *Candida saitoana* thus promotes the improvement of the significant parameters that are involved in the assessment of complexion brightness.

These different tests therefore show well the cosmetic effects of an active ingredient that is obtained from *Candida saitoana* and a cosmetic composition that includes it on the stimulation of the pathway of the autophagy as well as the consequences that follow therefrom on the detoxification of cells, and, visually, on the surface condition of the skin.

The invention claimed is:

1. A cosmetic method for activating the autophagy of skin cells, comprising applying to the skin an effective amount of a cosmetic active ingredient, the active ingredient being an enzymatic hydrolysate of *Candida saitoana* comprising carbohydrate compounds, at least a portion of the carbohydrates being alpha-glucan oligosaccharides having a molecular weight between 180 Da to 1500 Da.

2. The cosmetic method according to claim 1, wherein activating the autophagy of the skin cells comprises stimulating LC3 protein synthesis in said skin cells.

3. The cosmetic method according to claim 1, wherein the method comprises detoxification of said skin cells.

4. The cosmetic method according to claim 1, wherein the method comprises improving the complexion brightness and/or smoothing the skin microrelief.

5. A cosmetic process for personal care of human skin, comprising topically applying to the skin a composition comprising an effective amount of an active ingredient, the active ingredient being an enzymatic hydrolysate of *Candida saitoana* comprising carbohydrate compounds, at least a portion of the carbohydrates being alpha-glucan oligosaccharides having a molecular weight between 180 Da to 1500 Da,
wherein the effective amount improves the surface condition of dull and/or intoxicated skin.

6. A cosmetic process for personal care of the human skin, comprising topically applying to the skin a composition comprising an effective amount of an active ingredient, the active ingredient being an enzymatic hydrolysate of *Candida saitoana* comprising carbohydrate compounds, at least a portion of the carbohydrates being alpha-glucan oligosaccharides having a molecular weight between 150 Da to 1800 Da,
wherein the effective amount smoothes the microrelief of the skin and/or to improves complexion brightness.

7. The cosmetic method according to claim 1, wherein at least 20% of the carbohydrates are alpha-glucan oligosaccharides having a molecular weight of between 180 Da to 1500 Da.

8. The cosmetic method according to claim 1, wherein the carbohydrate compounds comprise:
50-60% monosaccharides in the form of glucose, mannose and N-acetyl glucosamine, and
40-50% oligosaccharides having a mean degree of polymerization of 5, of which 60-70% are α-glucan oligosaccharides and 30-40% are β-glucan oligosaccharides (β-1,3 and β-1,6).

* * * * *